(12) United States Patent
Goshoo et al.

(10) Patent No.: US 6,808,920 B2
(45) Date of Patent: Oct. 26, 2004

(54) MICROCHIP DEVICE FOR CHEMOTAXIS OBSERVATION

(75) Inventors: Yasuhiro Goshoo, Tokyo (JP); Takaaki Kuroiwa, Tokyo (JP)

(73) Assignee: Yamatake Corporation, Tokyo (JP)

( * ) Notice: Subject to any disclaimer, the term of this patent is extended or adjusted under 35 U.S.C. 154(b) by 0 days.

(21) Appl. No.: 10/352,122

(22) Filed: Jan. 28, 2003

(65) Prior Publication Data

US 2003/0170880 A1 Sep. 11, 2003

(30) Foreign Application Priority Data

Jan. 29, 2002 (JP) ........................................ 2002-019346

(51) Int. Cl.[7] .............................................. C12M 1/34
(52) U.S. Cl. .................... 435/288.5; 422/101; 422/102; 438/723; 438/724; 438/743; 216/2; 216/58; 216/67; 216/80
(58) Field of Search .............................. 422/68.1, 102, 422/101; 435/288.5; 438/71.9, 723, 724, 743; 216/2, 4, 58, 67, 80

(56) References Cited

U.S. PATENT DOCUMENTS 5,302,515 A * 4/1994 Goodwin, Jr. ................ 435/29
5,744,366 A * 4/1998 Kricka et al. ................. 436/63
6,238,874 B1 * 5/2001 Jarnagin et al. ............ 435/7.21
6,368,871 B1 * 4/2002 Christel et al. ............. 436/180
6,602,791 B2 * 8/2003 Ouellet et al. .............. 438/696
6,663,231 B2 * 12/2003 Lee et al. ..................... 347/68

FOREIGN PATENT DOCUMENTS

JP          2002-159287           6/2002

OTHER PUBLICATIONS

Nikkei Biotechnology & Business, pp. 48–50, "Real–Time Analysis of Chemotaxis of Cells", Nov. 2001 (with English translation).

* cited by examiner

*Primary Examiner*—David A. Redding
(74) *Attorney, Agent, or Firm*—Oblon, Spivak, McClelland, Maier & Neustadt, P.C.

(57) ABSTRACT

A microchip device for chemotaxis observation according to the present invention is provided with the first well in which chemotactic factors are to be filled, and the second well in which chemotactic cells are to be filled. There is provided a channel between the first well and the second well. The channel has a plurality of paths. A sidewall surfaces of the path is substantially perpendicular to a bottom surface, as formed by anisotropic dry etching.

2 Claims, 6 Drawing Sheets

MICROCHIP DEVICE FOR CHEMOTAXIS OBSERVATION

BACKGROUND OF THE INVENTION

1. Field of the Invention

The present invention relates to a microchip device for chemotaxis observation to observe a phenomenon called chemotaxis.

2. Related Background Art

Chemotaxis is a directional migration of cells in response to concentration gradients of chemical substances called chemotactic factors. The chemotaxis has been applied to development of therapeutic agents; especially, it is expected to open a new approach to development of cures for inflammation, allergy, and cancer. Chemotaxis studies therefore have increasing importance. In order to observe the chemotaxis, there is proposed use of a microchip for observing movement of the chemotactic factors. It is, for example, described in Nikkei Biotechnology & Business, November 2001: pp. 48–50.

The microchip, which will be referred to hereinafter as a microchip device for chemotaxis observation, is provided with a section in which chemotactic factors are to be filled, and a section in which chemotactic cells are to be filled. Between those sections are a number of narrow paths called a channel in a lattice arrangement. The width of the path is a little smaller than a general size of a cell. When concentration gradients of the chemotactic factors occur, cells move themselves toward a higher concentration through the paths. FIG. 8 shows a structure of a path in a conventional microchip device for chemotaxis observation. As shown in FIG. 8, a path 41 of the conventional microchip device is formed so that an island 42 stands as a sidewall thereof. A cross-sectional view along line B–B' is shown at the bottom of FIG. 8. As shown therein, the island 42 projects from a bottom surface of the path 41 at an obtuse angle of α. In other words, the sidewall surface of the path 41 has the obtuse angle α to the bottom surface. The angle α is 54.7°, for example.

In the conventional microchip device for chemotaxis observation, however, the sidewall surface of the path 41 is sloped; thus, a slope 421 appears to be black when examining the chemotaxis with a microscope. The conventional microchip device for chemotaxis observation therefore has the problem that observation of the cells passing through the slope 421 is interfered with. Also, it has a problem that there is a limitation to the width of the path because narrower path causes restriction of the depth due to the slope.

SUMMARY OF THE INVENTION

As explained above, the conventional microchip device for chemotaxis observation has the problem that the slope of the sidewall surface of the path interferes with the cell observation and restricts the path width.

The present invention has been accomplished to solve the above problems and an object of the present invention is thus to provide a microchip device for chemotaxis observation which facilitates the cell observation and allows design freedom for the path width.

A microchip device for chemotaxis observation according to the present invention is provided with a first area in which chemotactic factors are to be filled, a second area in which chemotactic cells are to be filled, and a channel having a path communicating between the first area and the second area, wherein a sidewall surface of the path is substantially perpendicular to a bottom surface of the path.

The above path is configured by anisotropic dry etching in order to form the sidewall surface substantially perpendicular to the bottom surface of the path. The sidewall surface of the path is thus not sloped; therefore, it does not interfere with the observation. Besides, the anisotropic dry etching makes it possible to form paths of various shapes including circular, elliptical, triangular, and L-shape, as well as linear shape. It is also makes it possible to form a path having the width that is so microscopic as to be defined by a photomask, thereby enabling observation of smaller cells and miniaturization of the microchip. Further, the dry etching provides high repeatability while wet etching has low repeatability to produce various amount of side etching.

The anisotropic dry etching is preferably inductively coupled plasma reactive ion etching (ICP-RIE).

In a preferred embodiment, the microchip device for chemotaxis observation is composed of a silicon wafer.

A manufacturing method of a microchip device for chemotaxis observation according to the present invention is a method of manufacturing a microchip device for chemotaxis observation provided with a first area in which chemotactic factors are to be filled, a second area in which chemotactic cells are to be filled, and a channel having a path communicating between the first area and the second area, wherein the channel is formed by anisotropic dry etching. A sidewall surface of the path formed by the anisotropic dry etching is not sloped; therefore, it does not interfere with the observation. Besides, the anisotropic dry etching makes it possible to form paths of various shapes including circular, elliptical, triangular, and L-shape, as well as linear shape. It is also makes it possible to form a path having the width that is so microscopic as to be defined by a photomask, thereby enabling observation of smaller cells and miniaturization of the microchip. Further, the dry etching provides high repeatability while wet etching has low repeatability to produce various amount of side etching.

The microchip device for chemotaxis observation is provided with a penetration hole through which the chemotactic factors and the chemotactic cells are filled. The penetration hole is preferably formed by the anisotropic dry etching. It solves the problem that etching damages a wall surface of the penetration hole to injure cells, thereby allowing effective experiments. It also facilitates alignment of the penetration hole to simplify manufacturing processes.

The anisotropic dry etching is preferably inductively coupled plasma reactive ion etching.

The present invention will become more fully understood from the detailed description given hereinbelow and the accompanying drawings which are given by way of illustration only, and thus are not to be considered as limiting the present invention.

DESCRIPTION OF THE PREFERRED EMBODIMENTS

The inventors of the present invention focused on that a slope of a sidewall surface of a path interferes with observation in a conventional microchip device for chemotaxis observation. As a result, they have found, for one thing, that a microchip devices for easier observation of chemotaxis can be obtained by forming a sidewall surface substantially perpendicular to a bottom surface of a path. In order to have the above configuration, for next thing, they have improved the manufacturing processes by employing an anisotropic dry etching process instead of a wet etching process that has been conventionally used. The dry etching process can eliminate a cleaning step, which is required in the wet etching process, thereby saving time and producing the microchip effectively.

In the following, a preferred embodiment of the present invention will be explained in detail with reference to the drawings.

Figure 1:
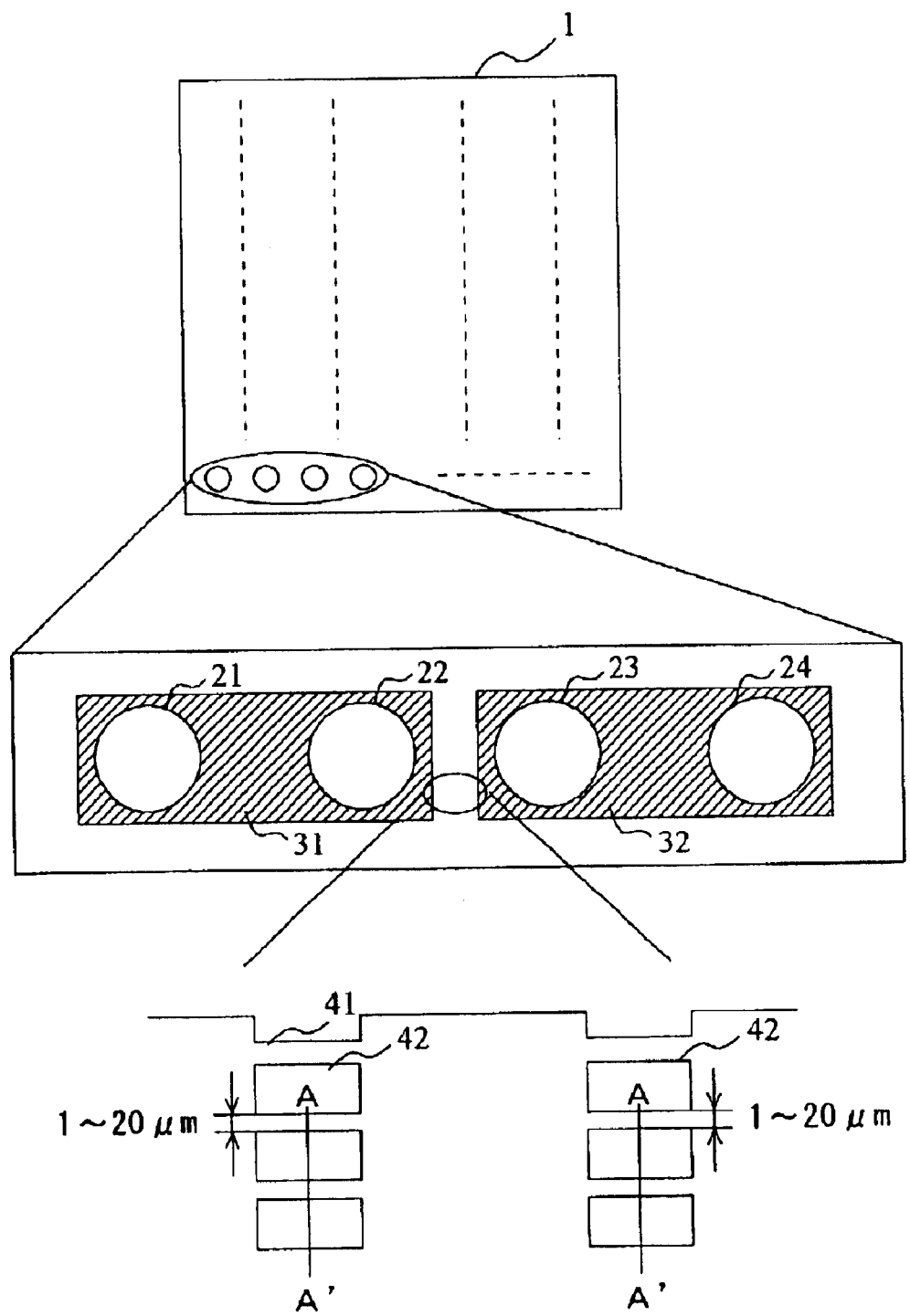
FIG. 1 is a diagram to show a structure of a microchip device for chemotaxis observation according to the present invention.

FIG. 1 shows a structure of a microchip device for chemotaxis observation according to a preferred embodiment of the present invention. As shown therein, a microchip device 1 for chemotaxis observation according to the present embodiment is composed of a quadrilateral flat plate of silicon wafer, with length and breadth of 50 to 200 mm respectively. The microchip device 1 for chemotaxis observation is provided with a plurality of penetration holes.

The penetration holes consists of a set of four adjacent penetration holes 21, 22, 23, and 24. A well 31 that is an area surrounding the penetration holes 21 and 22, and a well 32 that is an area surrounding the penetration holes 23 and 24 are configured to be lower than adjacent region by 10 to 400 $\mu$m. The well 31 is the area in which chemotactic factors are to be filled, and the well 32 is the area in which chemotactic cells are to be filled. The well 31 and the well 32 range with a certain distance away from each other.

There is provided a channel 4 between the well 31 and the well 32. The channel 4 consists of a path 41 and an island 42 which constitutes a sidewall surface of the path 41. In the case here, two of the paths 4 are provided, and the paths 4 are respectively provided with a plurality of the paths 41. The width of the path 41 is approximately 1 $\mu$m to 20 $\mu$m, a little smaller than a general size of a cell.

Figure 2:
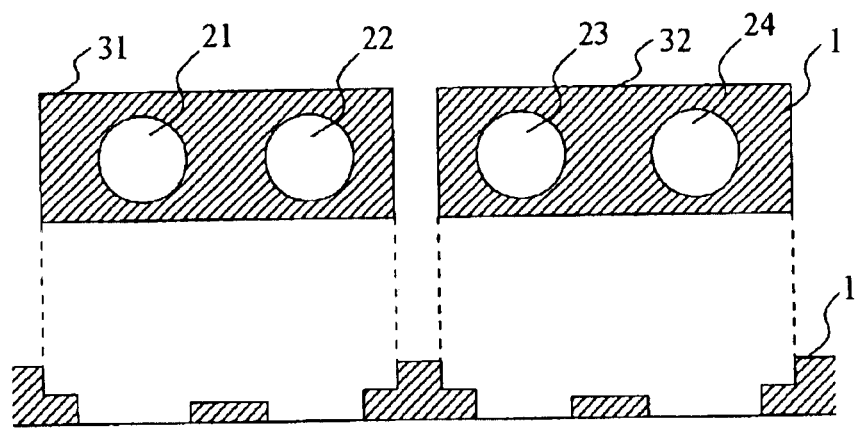
FIG. 2 is a diagram to show a part of the microchip device for chemotaxis observation according to the present invention.

FIG. 2 is a top view of the well 31 and the well 32, and a side view of the penetration hole 21, 22, 23, and 24.

Figure 3:
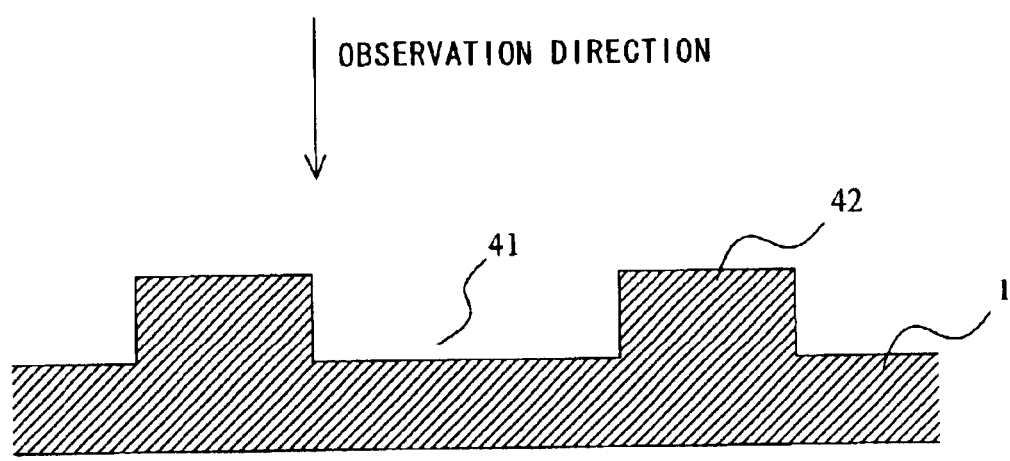
FIG. 3 is a diagram to show another part of the microchip device for chemotaxis observation according to the present invention.
Figure 8:
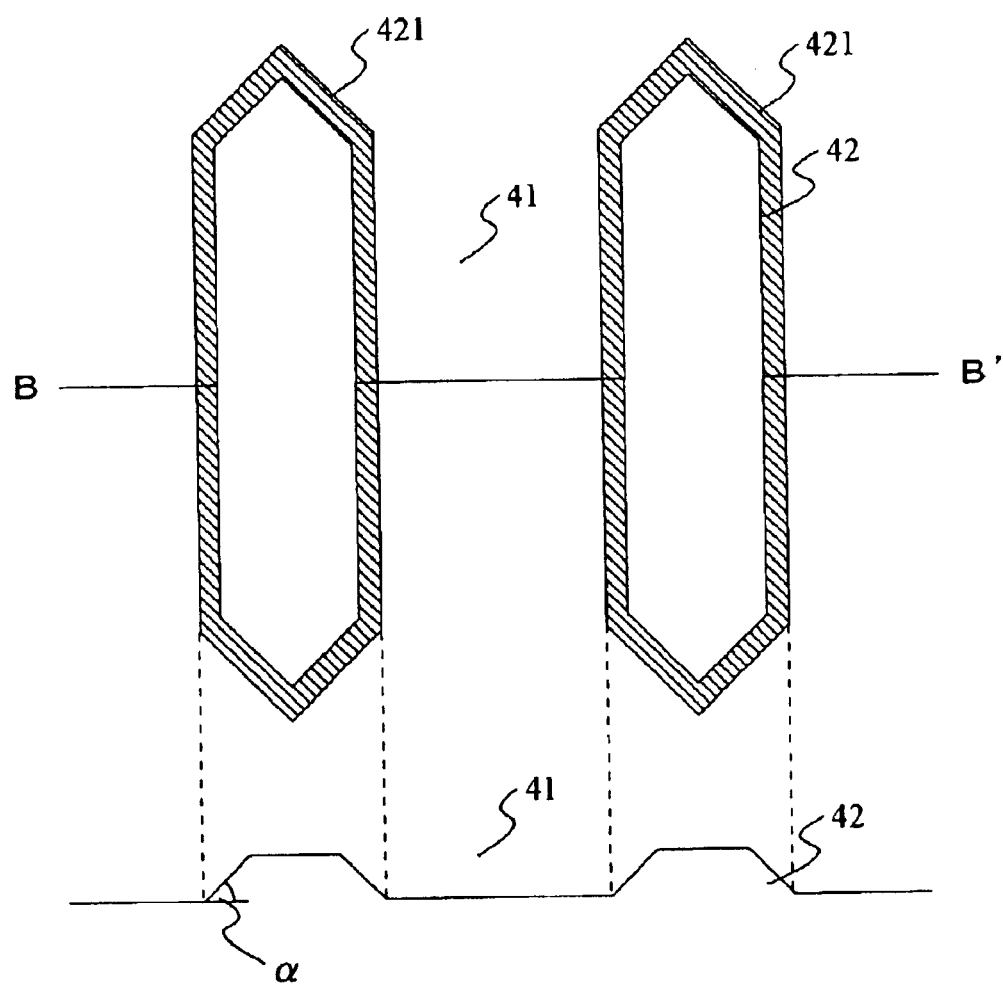
FIG. 8 is a diagram to show a structure of a conventional microchip device for chemotaxis observation.

FIG. 3 is a cross-sectional view of the channel 4 along line A–A' in FIG. 1. As shown in FIG. 3, a sidewall surface of the path 41 formed on the island 42 is substantially perpendicular to a bottom surface, which is different from the conventional microchip device for chemotaxis observation shown at the bottom of FIG. 8. The sidewall surface of the path 41 is therefore substantially parallel to an observation direction. An angle between the sidewall surface and the bottom surface is such a degree that does not cause a problem in observation, and it is preferably 90 plus or minus 10 degrees. A height of the island 42, that is, a height of the sidewall of the path 41 is approximately 4.5 $\mu$m.

Figure 4:
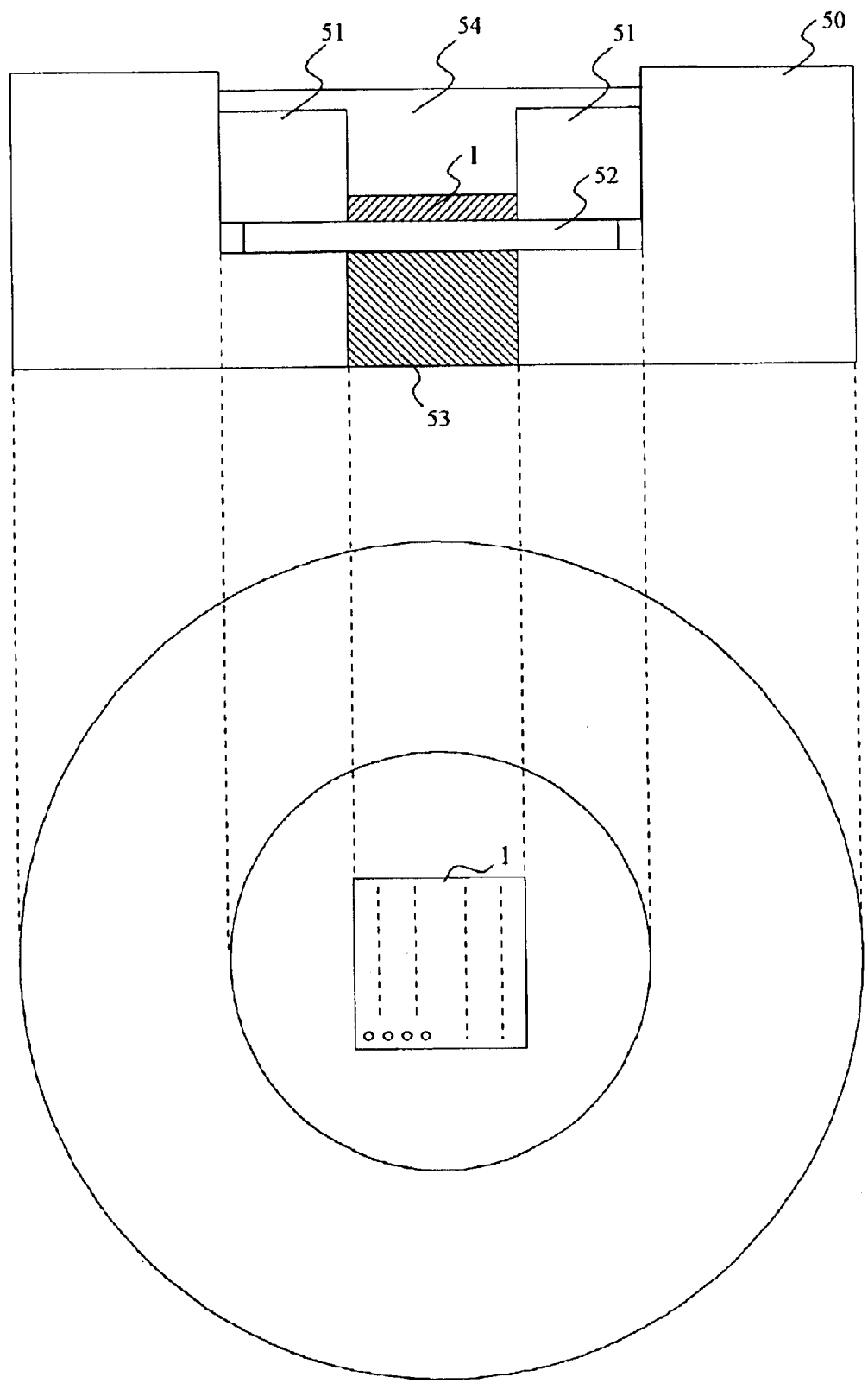
FIG. 4 is a diagram to show the microchip device for chemotaxis observation according to the present invention being built into jigs necessary for observation.

A structure where the microchip device 1 for chemotaxis observation is built into necessary jigs will be explained hereinafter with reference to FIG. 4 and FIG. 5. As shown in Figs., the jigs include a main jig 50 having a circular groove and a penetration hole 53 in its central part, a glass plate fixing jig 51 to fix a glass plate 52, a microchip fixing jig 55 to fix the microchip device 1 for chemotaxis observation, and an auxiliary jig 56 to fix the microchip fixing jig 55 to the main jig 50. The jigs 50, 51, 55, and 56 are composed of Steel Use Stainless (SUS), for example. As the glass plate 52, a glass plate of 1 mm in thickness is generally used.

The circular groove formed in the central part of the main jig 50 has such a shape that the glass plate fixing jig 51 is mounted therein. The penetration hole 53 in the main jig 50, which is provided for observation of chemotaxis, has the same shape as a microchip, that is, a quadrilateral penetration hole.

The glass plate fixing jig 51 is provided in its center with a penetration hole in which the microchip device 1 for chemotaxis observation is mounted. The penetration hole has the same shape as the microchip, that is, a quadrilateral penetration hole. There is embedded in the glass plate fixing jig 51 an O-Ring that is made up of rubber, so as to absorb shock at the glass plate 52.

Figure 5:
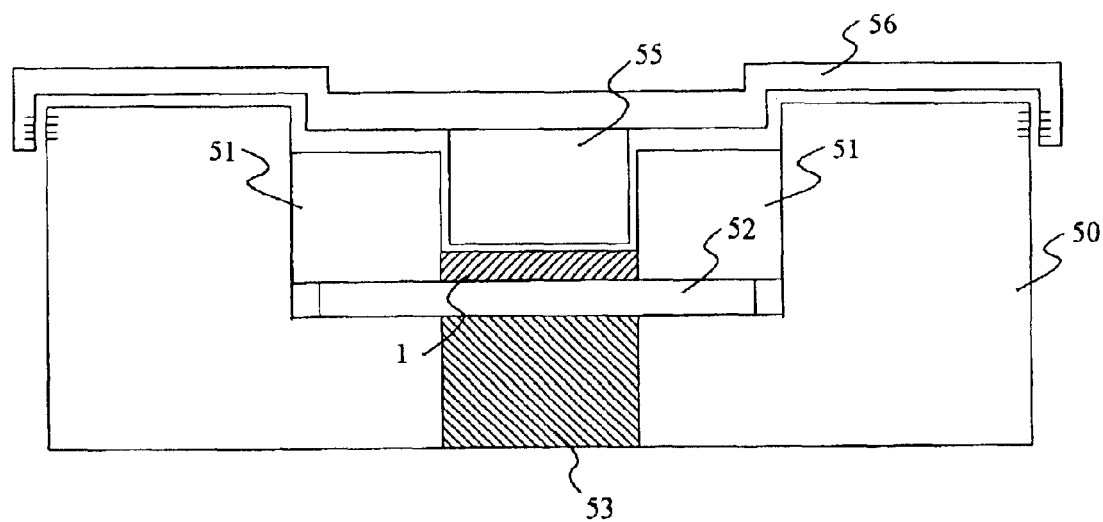
FIG. 5 is a diagram to show the microchip device for chemotaxis observation according to the present invention being built into jigs necessary for observation.

The microchip fixing jig 55 has, as shown in FIG. 5, a shape which can be inserted into the penetration hole of the glass plate fixing jig 51, that is, a cube. The microchip fixing jig 55 is provided with a plurality of penetration holes passing from its top face to bottom face. The penetration holes are arranged in the positions respectively corresponding to the penetration holes 21, 22, 23, and 24 in the microchip device 1 for chemotaxis observation in a condition where the microchip fixing jig 55 is placed on the microchip device 1 for chemotaxis observation. They are therefore provided in the same number and the same position as the penetration holes 21 to 24 in the microchip device 1 for chemotaxis observation. In this configuration, it is possible to pour liquid and so on into the penetration holes 21 to 24 when the microchip fixing jig 55 is placed on the microchip device 1 for chemotaxis observation.

The auxiliary jig 56 is provided in its both ends thread cuttings which can be fit with thread cuttings provided for a periphery of the main jig 50 so as to hold down to fix the microchip fixing jig 55. Therefore, if rotating the auxiliary jig 56, it moves the microchip fixing jig 55 downward, that is, moves the microchip device 1 for chemotaxis observation in a direction to bring it into contact with the glass plate 52.

Figure 6:
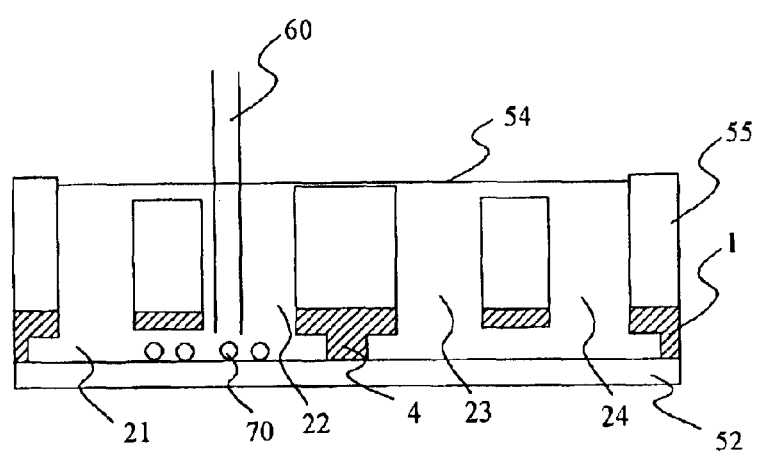
FIG. 6 is a diagram to explain preparation for observation with the microchip device for chemotaxis observation according to the present invention.

Now, an explanation will be given of how to use the microchip device 1 for chemotaxis observation with reference to FIG. 6. First, enter cells 70 such as leukocytes into the penetration hole 22 with a micro-syringe, to arrange them around an entrance of the path 41 of the channel 4. Next, pour a small amount of chemotactic factors into the penetration hole 23 with a micro-syringe, for example. The cells 70 then migrate by chemotaxis to pass through the path 41 of the channel 4. Observe the migration of the cells over a period of one hour, for example.

A manufacturing flow chart to form a channel on the microchip device 1 for chemotaxis observation will be explained hereinbelow with reference to FIGS. 7A to 7F.

Figure 7A:
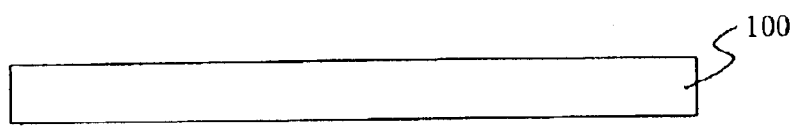
FIGS. 7A, 7B, 7C, 7D, 7E, and 7F are diagrams to show a manufacturing flow chart of the microchip device for chemotaxis observation according to the present invention.
Figure 7B:
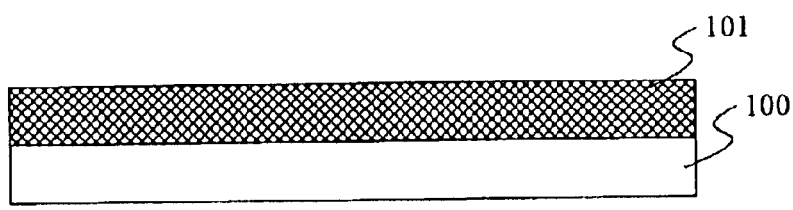
Figure 7C:
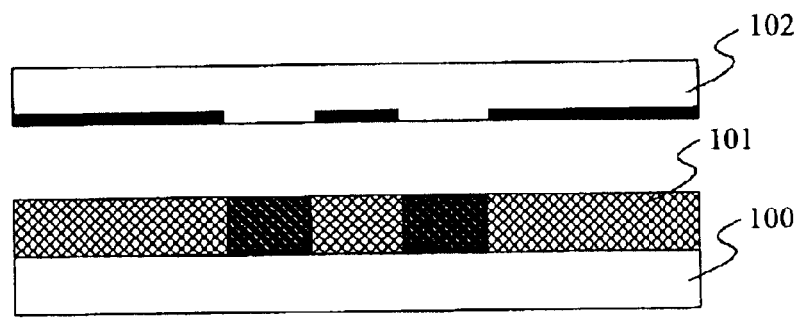
Figure 7D:
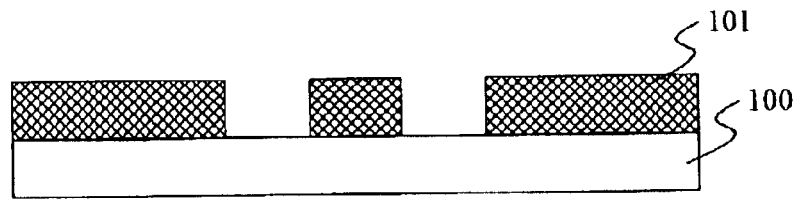
Figure 7E:
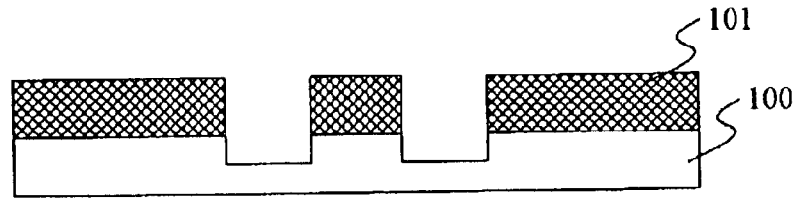
Figure 7F:

First, prepare a silicon wafer 100 as shown in FIG. 7A. Next, form a resist 101 over the silicon wafer 100 by spin coating for example, as in FIG. 7B. A positive resist made of Tokyo Ohka Kogyo Co., Ltd., for example, is used for the resist 101. Then, expose the resist 101 to ultraviolet light through a mask 102 as in FIG. 7C. The mask 102 has such a configuration that the ultraviolet light passes through only the prescribed area thereof. On the resist 101, the area which has been exposed to the ultraviolet light is deteriorated. Further, develop the resist with a developer, and remove only the deteriorated area, as in FIG. 7D. The processes shown in FIGS. 7B, 7C, and 7D are called a photolithography process.

After that, carry out inductively coupled plasma reactive ion etching by an ICP-RIE device. The inductively coupled plasma reactive ion etching, one of dry etchings, etches a substrate by synergic effect of perpendicular incidence of ions in plasma and reaction of activated species. The etching is anisotropic dry etching, and both physical reaction and chemical reaction occur therein.

The above explained photolithography process and etching process are repeated three times in order to form the microchip device 1 for chemotaxis observation according to the preferred embodiment of the present invention.

The sidewall surface of the path formed by the anisotropic dry etching is not sloped; therefore, it does not interfere with the observation. Besides, the anisotropic dry etching makes it possible to form paths of various shapes including circular, elliptical, triangular, and L-shape, as well as linear shape. It is also makes it possible to form a path having the width that is so microscopic as to be defined by a photomask, thereby enabling observation of smaller cells and miniaturization of the microchip. Further, the dry etching provides high repeatability while wet etching has low repeatability to produce various amount of side etching.

Though a conventional technique has been used a sandblasting method for formation of penetration holes of a microchip device for chemotaxis observation, the preferred embodiment of the present invention employs a dry etching method of ICP-RIE to form the penetration holes. It has solved the problem that etching damages a wall surface of the penetration hole to injure cells, thereby allowing effective experiments. It also facilitates alignment of the penetration hole to simplify manufacturing processes.

While the ICP-RIE is employed as an example of the anisotropic dry etching in the above-mentioned embodiment, the present invention is not restricted thereto, whereas other anisotropic dry etchings may be employed, such as sputtering etching, sputtering ion beam etching, and reactive ion beam etching.

Also, though the above-mentioned embodiment explains a case where the microchip device for chemotaxis observation is composed of a silicon wafer, the material used is not limited thereto. For example, the microchip device for chemotaxis observation can be composed of glass or plastic. If the glass is used, it is processed by sputtering etching for example. If the plastic is used, on the other hand, it is processed by injection molding or stamping for example.

As explained in the foregoing, the present invention provides a microchip device for chemotaxis observation which facilitates cell observation and allows design freedom for path width.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A manufacturing method of a microchip device for chemotaxis observation, comprising:

forming a first area in a substrate in which chemotactic factors are to be filled;

forming a second area in the substrate in which chemotactic cells are to be filled;

forming a channel having at least one path communicating between the first area and the second area in the substrate;

forming a first penetration hole in the substrate through which the chemotactic factors are filled in the first area; and forming a second penetration hole in the substrate through which the chemotactic cells are filled in the second area, wherein the step of forming a channel, the step of forming a first penetration hole, and the step of forming a second penetration hole include anisotropic dry etching.

2. A manufacturing method of a microchip device for chemotaxis observation according to claim 1, wherein the anisotropic dry etching is inductively coupled plasma reactive ion etching.

* * * * *